United States Patent
Bauer et al.

(10) Patent No.: US 7,956,210 B2
(45) Date of Patent: Jun. 7, 2011

(54) IRIDIUM-CATALYZED PRODUCTION METHOD FOR ORGANOSILICON COMPOUNDS

(75) Inventors: Andreas Bauer, Kirchdorf (DE); Oliver Schäfer, Burghausen (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 12/528,899

(22) PCT Filed: Feb. 25, 2008

(86) PCT No.: PCT/EP2008/052237
§ 371 (c)(1),
(2), (4) Date: Oct. 12, 2009

(87) PCT Pub. No.: WO2008/107332
PCT Pub. Date: Sep. 12, 2008

(65) Prior Publication Data
US 2010/0022793 A1 Jan. 28, 2010

(30) Foreign Application Priority Data
Mar. 7, 2007 (DE) .................... 10 2007 011 158

(51) Int. Cl.
*C07F 7/08* (2006.01)

(52) U.S. Cl. .................................................. 556/479
(58) Field of Classification Search ................. None
See application file for complete search history.

(56) References Cited

U.S. PATENT DOCUMENTS

| | | | |
|---|---|---|---|
| 2,823,218 A | 2/1958 | Speier et al. | |
| 3,159,601 A | 12/1964 | Ashby | |
| 3,296,291 A | 1/1967 | Chalk et al. | |
| 3,564,266 A | 2/1971 | Klotz | |
| 4,658,050 A | 4/1987 | Quirk et al. | |
| 5,616,762 A | 4/1997 | Kropfgans et al. | |
| 6,359,161 B2 * | 3/2002 | Tonomura et al. | 556/479 |
| 2002/0052520 A1 | 5/2002 | Bauer et al. | |

FOREIGN PATENT DOCUMENTS

| | | |
|---|---|---|
| DE | 100 53 037 C1 | 1/2002 |
| EP | 0709392 A1 | 5/1996 |
| EP | 1156052 A2 | 11/2001 |
| JP | 06100572 A | 4/1994 |
| JP | 07126271 A | 5/1995 |

* cited by examiner

*Primary Examiner* — Sudhakar Katakam
(74) *Attorney, Agent, or Firm* — Brooks Kushman P.C.

(57) ABSTRACT

Alkyl silanes are prepared by silylating an unsaturated hydrocarbon with an Si—H functional silane employing an iridium chloride coordination compound as a catalyst and a polymeric polyene as a cocatalyst. Reaction bottoms can be worked up to provide an iridium-containing composition which remains catalytically active.

16 Claims, No Drawings

IRIDIUM-CATALYZED PRODUCTION METHOD FOR ORGANOSILICON COMPOUNDS

CROSS-REFERENCE TO RELATED APPLICATION

This application is the U.S. national phase of PCT Appln. No. PCT/EP2008/052237 filed Feb. 25, 2008 which claims priority to German application DE 10 2007 011 158.6 filed Mar. 7, 2007.

BACKGROUND OF THE INVENTION

1. Field of the Invention

The invention relates to a process for preparing substituted alkylsilanes by addition of silanes having an Si—H bond onto unsaturated aliphatics in the presence of a specific Ir catalyst/cocatalyst system.

2. Description of the Related Art

Substituted alkylsilanes are of tremendous economic interest for many fields. They are used, for example, as bonding agents or as crosslinkers.

The platinum- or rhodium-catalyzed hydrosilylation of unsaturated compounds has already been examined many times. The use of platinum-containing hydrosilylation catalysts is described, for example, in U.S. Pat. Nos. 2,823,218 A and 3,159,601. U.S. Pat. Nos. 3,296,291 A and 3,564,266 A mention the use of rhodium catalysts. The product yields are often very low at 20-45%, which can be attributed to considerable secondary reactions.

According to U.S. Pat. No. 4,658,050 A, JP 6100572 A and EP 0709392 A, iridium catalysts are used in the hydrosilylation of allyl compounds by alkoxy-substituted silanes. The Japanese patent JP 07126271 A is concerned with the hydrosilylation of allyl halides by chlorodimethylsilane. Disadvantages of these processes are either moderate yields, an uneconomically high catalyst concentration and/or a very short catalyst life. DE 10053037 C and EP 1156052 A describe processes in which low molecular weight, preferably cyclic dienes are added as cocatalysts in order to reduce the amounts of catalyst required. However, these cocatalysts have the disadvantage that they also react with the corresponding silanes and these reaction products are difficult to separate off from the desired target products by distillation.

A further disadvantage of these systems is that the reaction bottoms after conclusion of the reaction are contaminated with noble metal residues and a further isolation/concentration of the residues by extraction or precipitation cannot be carried out commercially, so that the reaction bottoms have to be worked up in their entirety.

SUMMARY OF THE INVENTION

It was therefore an object of the invention to develop a catalyst system which has a longer life and ensures high product yields and product purity with very small amounts of catalyst, and also allows the reaction to be carried out either continuously or batchwise. In addition, the reaction bottoms should be able to be reused without further work-up. These and other objects are achieved through the use of specific iridium chloride coordination compounds in the presence of specific polymeric cocatalysts containing minimally three ethylenic unsaturated moieties, preferably a polybutadiene.

DETAILED DESCRIPTION OF THE PREFERRED EMBODIMENTS

The invention provides a process for preparing silanes of the general formula I

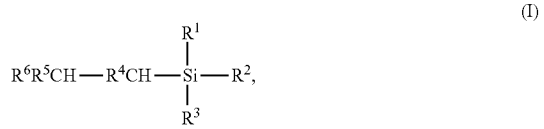
(I)

which comprises reacting compounds of the general formula II

(II)

with alkenes of the general formula III

(III), in the presence of an iridium compound of the general formula IV

(IV), where "en" is an open-chain, cyclic or bicyclic compound having at least one double bond of the general formula V

(V)

as catalyst and in the presence of polymeric cocatalysts comprising structural units of the general formulae VI VIII cis double bonds

(VI)

trans double bonds

(VII)

lateral double bonds

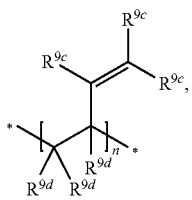
(VIII)

where
R$^1$, R$^2$, R$^3$ are each a hydrocarbon, chlorine or an alkoxy radical which may be unsubstituted or substituted by F, Cl or Br and has from 1 to 18 carbon atoms, where the carbon chain can be interrupted by nonadjacent —O— groups, R$^4$, R$^5$, R$^6$ are each hydrogen or a hydrocarbon radical which may be unsubstituted or substituted by F, Cl, OR, NR'$_2$, CN or NCO and having from 1 to 18 carbon atoms, where the carbon chain can be interrupted by nonadjacent —O— groups, where 2 or 3 radicals selected from among R$^4$, R$^5$, R$^6$ can together form a cyclic compound, R$^7$ is hydrogen or a hydrocarbon radical which may be unsubstituted or substituted by F, Cl, OR, NR'$_2$, CN or NCO and has from 1 to 18 carbon atoms, where the carbon chain can be interrupted by nonadjacent —O— groups, where 2 radicals R$^7$ can together form a cyclic compound, R$^8$ is hydrogen or a hydrocarbon radical which may be unsubstituted or substituted by F, Cl, OR, NR'$_2$, CN or NCO and has from 1 to 1000 carbon atoms, where the carbon chain can be interrupted by nonadjacent —O— groups, R$^{9a}$, R$^{9b}$, R$^{9c}$, R$^{9d}$ are each hydrogen or a hydrocarbon radical which may be unsubstituted or substituted by F, Cl, OR, NR'$_2$, CN or NCO and having from 1 to 18 carbon atoms, where the carbon chain can be interrupted by nonadjacent —O— groups, where 2 or 3 radicals selected from among R$^{9a}$, R$^{9b}$, R$^{9c}$, R$^{9d}$ can together form a cyclic compound, R' is hydrogen or a hydrocarbon radical which may be unsubstituted or substituted by F, Cl or Br and having from 1 to 18 carbon atoms, where the carbon chain can be interrupted by nonadjacent —O— groups, l, m are integers from 3 to 5000 and
n is an integer from 5 to 5000, and wherein "*" is a terminal group of the polymeric cocatalyst.

The catalyst system comprising the iridium compound of the general formula IV and polymeric cocatalysts having structural units of the general formulae VI-VIII has a long life, ensures high product yields and product purity at very small amounts of catalyst and allows the reaction to be carried out either continuously or batchwise. Noble metal residues can easily be removed from the reaction bottoms.

The silanes of the general formula I are usually formed in yields of at least 95%. The crude products of the general formula I which are prepared in this way by the process of the invention are obtained in a purity of up to 98%, so that, depending on the field of use, a work-up by distillation may even be able to be dispensed with. After the products of the general formula I have been separated off by distillation, the distillation bottoms can be reused for a reaction without further work-up.

The hydrocarbon radicals R$^1$, R$^2$, R$^3$ are preferably alkyl, alkenyl, cycloalkyl, aryl radicals or Cl. The hydrocarbon radicals R$^1$, R$^2$, R$^3$ preferably do not have any substituents. The hydrocarbon radicals R$^1$, R$^2$, R$^3$ preferably have from 1 to 6 carbon atoms. Particularly preferred radicals are methyl, ethyl, propyl and phenyl. Preferred alkoxy radicals have from 1 to 6 carbon atoms. Particularly preferred radicals are methyl, ethyl, propyl and Cl.

The hydrocarbon radicals R$^4$, R$^5$, R$^6$ are preferably alkyl, alkenyl, cycloalkyl or aryl radicals. The substituents on the hydrocarbon radicals R$^4$, R$^5$, R$^6$ are preferably chlorine or bromine. The hydrocarbon radicals R$^4$, R$^5$, R$^6$ preferably have from 1 to 10 carbon atoms. Particularly preferred radicals are methyl, chloroethyl, propyl and phenyl. The cyclic compound formed by R$^4$, R$^5$, R$^6$ preferably has from 5 to 15 carbon atoms.

The hydrocarbon radicals R$^7$ are preferably alkyl, alkenyl, cycloalkyl or aryl radicals. The hydrocarbon radicals R$^7$ preferably do not have any substituents. The hydrocarbon radicals R$^7$ preferably have from 1 to 10 carbon atoms. Particularly preferred radicals are methyl, ethyl, propyl and phenyl. The cyclic compound formed from 2 radicals R$^7$ preferably has from 5 to 15 carbon atoms.

The hydrocarbon radicals R$^8$ are preferably alkyl, alkenyl, cycloalkyl or aryl radicals. The hydrocarbon radicals R$^8$ preferably do not have any substituents. The hydrocarbon radicals R$^8$ preferably have at least 2, in particular at least 5 carbon atoms, and preferably have not more than 200, in particular not more than 100 carbon atoms.

The hydrocarbon radicals R$^{9a}$, R$^{9b}$, R$^{9c}$, R$^{9d}$ are preferably alkyl, alkenyl, cycloalkyl or aryl radicals. The hydrocarbon radicals R$^{9a}$, R$^{9b}$, R$^{9c}$, R$^{9d}$ preferably do not have any substituents. The hydrocarbon radicals R$^{9a}$, R$^{9b}$, R$^{9c}$, R$^{9d}$ preferably have from 1 to 10 carbon atoms. Particularly preferred radicals are methyl, ethyl, propyl and phenyl. The cyclic compound formed from R$^{9a}$, R$^{9b}$, R$^{9c}$, R$^{9d}$ preferably has from 5 to 15 carbon atoms.

The hydrocarbon radicals R' are preferably alkyl, alkenyl, cycloalkyl or aryl radicals. The hydrocarbon radicals R' preferably do not have any substituents. The hydrocarbon radicals R' preferably have from 1 to 6 carbon atoms. Particularly preferred radicals are methyl, ethyl, propyl and phenyl.

Preference is given to l, m being integers of at least 6, in particular at least 20 and not more than 2000, and in particular not more than 200.

Preference is given to n being an integer of at least 10, in particular at least 50 and not more than 1000, and in particular not more than 200.

The compound of the general formula II is preferably reacted in an excess of from 0.01 to 100 mol % of II, more preferably from 0.1 to 10 mol %, with an alkene of the general formula III. The iridium compound of the general formula IV is preferably used in a concentration of from 5 to 250 ppm, in particular from 10 to 50 ppm. The polymeric cocatalyst is preferably used in a concentration of from 50 to 50,000 ppm, in particular from 50 to 20,000 ppm.

The "en" compound in the general formula IV preferably has two double bonds which are most preferably not conjugated. Particular preference is given to using a cyclic "en" compound. In a very particularly preferred case, [(cycloocta-1C,5C-diene)IrCl]$_2$ is used as catalyst.

The polymeric cocatalyst can be conjugated or nonconjugated. Particularly preferred polymeric cocatalysts are polybutadienes having a molecular weight of from 200 to 200,000 g/mol, more preferably a molecular weight of from 500 to 20,000 g/mol and most preferably a molecular weight of from 1000 to 10,000 g/mol. Particular preference is likewise given to polymeric cocatalysts in which the proportion of structural units of the general formula VI (cis double bond) is at least 10% by weight, most preferably at least 20% by weight. Examples of such compounds are the Lithene® products from Synthomer, e.g. Lithene® N4-5000 polymer.

For example, the reaction components of the general formula II together with the iridium catalyst of the general formula IV and, if desired, the polymeric cocatalyst are placed in a reaction vessel and the reaction components of the general formula III, if desired in admixture with the polymeric cocatalyst, are introduced while stirring. The reaction can, if appropriate, occur in solution in the target product of the general formula I. In another variant, the target product of the general formula I together with catalyst and, if desired, polymeric cocatalyst are placed in a reaction vessel and a mixture of component II, III and, if desired, the polymeric cocatalyst is introduced.

The reaction time to be employed is preferably from 0.1 to 2000 minutes. The reaction is preferably carried out at a temperature of from 0 to 300° C., in particular from 20° C. to 200° C. The use of superatmospheric pressure may also be useful, preferably up to 100 bar.

All symbols in the above formulae have their meanings independently of one another.

In the following examples, all amounts and percentages are, unless indicated otherwise, by weight, all pressures are 0.10 MPa (abs.) and all temperatures are 20° C.

EXAMPLE C1

Not According to the Invention 19.2 g (0.25 mol) of allyl chloride, 0.1 g (9.2×10$^{-4}$ mol) of 1,5-cyclooctadiene and 3.0 mg (4.5 ×10$^{-6}$ mol, 18 ppm) of di-µ-chlorobis[(cyclooctа-1C,5C-diene)iridium(I)] were placed in a 100 ml three-neck flask provided with a low-temperature condenser, internal thermometer and dropping funnel. At a bath temperature of 37° C., a mixture of 23.7 g (0.25 mol) of chlorodimethylsilane and 0.1 g (9.2×10$^{-4}$ mol) of 1,5-cyclooctadiene was added over a period of 1.5 hours at such a rate that the internal temperature did not exceed 45° C. To complete the reaction, the mixture was maintained at a bath temperature of 45° C. for a further one hour. Work-up by distillation gave 40.8 g of chloro(3-chloropropyl)dimethylsilane, corresponding to a yield of 95% based on the silane.

The distillation bottoms were no longer catalytically active and could not be used in a further reaction, but instead had to be worked up directly to recover iridium.

EXAMPLE 2

13.8 g (0.18 mol) of allyl chloride, 0.28 g (1% by weight based on the total amount) of Lithene® N4-5000 (from Chemetall) and 2.0 mg (3.0×10$^{-6}$ mol, 40 ppm w/w of Ir based on the total amount) of di-µ-chlorobis[(cyclooctа-1C,5C-diene) iridium(I)] were placed in a 100 ml three-neck flask provided with a low-temperature condenser, internal thermometer and dropping funnel. At a bath temperature of 40° C., 14.2 g (0.15 mol) of chlorodimethylsilane were introduced over a period of 40 minutes at such a rate that the internal temperature did not exceed 45° C. To complete the reaction, the mixture was maintained at a bath temperature of 45° C. for a further one hour. Work-up by distillation gave 24.4 g of chloro(3-chloropropyl)dimethylsilane, corresponding to a yield of 95.5% based on the silane. The distillation bottoms could be reused without further work-up for an additional product synthesis, without more Lithene® N4-5000 or iridium catalyst having to be added.

The invention claimed is:

1. A process for preparing silanes of the formula I

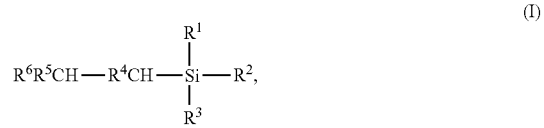

which comprises reacting compounds of the formula II

with alkenes of the formula III

in the presence of at least one iridium compound catalyst of the formula IV

where "en" is an open-chain, cyclic or bicyclic compound having at least one double bond of the formula V

in the presence of at least one polymeric cocatalysts comprising structural units of the formulae VI-VIII cis double bonds

trans double bonds

where

R$^1$, R$^2$, R$^3$ are each individually a hydrocarbon, chlorine, or an alkoxy radical optionally substituted by F, Cl or Br, having from 1 to 18 carbon atoms optionally interrupted by nonadjacent —O— groups, R$^4$, R$^5$, R$^6$ are each individually hydrogen or a hydrocarbon radical optionally substituted by F, Cl, OR, NR'$_2$, CN or NCO and having from 1 to 18 carbon atoms optionally interrupted by nonadjacent —O— groups, where 2 or 3 radicals $R^4$, $R^5$, $R^6$ optionally form a cyclic compound, $R^7$ is hydrogen or a hydrocarbon radical optionally substituted by F, Cl, OR, $NR'_2$, CN or NCO and has from 1 to 18 carbon atoms optionally interrupted by nonadjacent —O— groups, where 2 radicals $R^7$ optionally form a cyclic compound, $R^8$ is hydrogen or a hydrocarbon radical optionally substituted by F, Cl, OR, $NR'_2$, CN or NCO and has from 1 to 1000 carbon atoms optionally interrupted by nonadjacent —O— groups, $R^{9a}$, $R^{9b}$ are each hydrogen or a hydrocarbon radical optionally substituted by F, Cl, OR, $NR'_2$, CN or NCO and having from 1 to 18 carbon atoms optionally interrupted by nonadjacent —O— groups, where two or three radicals $R^{9a}$, $R^{9b}$, $R^{9c}$, $R^{9d}$ optionally form a cyclic compound, R' is hydrogen or a hydrocarbon radical optionally substituted by F, Cl or Br and having from 1 to 18 carbon atoms optionally interrupted by nonadjacent —O— groups, l, m are integers from 3 to 5000.

2. The process of claim 1, wherein the hydrocarbon radicals $R^7$ are selected from the group consisting of methyl, ethyl, propyl, phenyl, and mixtures thereof.

3. The process of claim 1, wherein the hydrocarbon radicals $R^8$ have at least 5 carbon atoms.

4. The process of claim 2, wherein the hydrocarbon radicals $R^8$ have at least 5 carbon atoms.

5. The process of claim 1, wherein the hydrocarbon radicals $R^{9a}$, $R^{9b}$ have from 1 to 10 carbon atoms.

6. The process of claim 2, wherein the hydrocarbon radicals $R^{9a}$, $R^{9b}$ have from 1 to 10 carbon atoms.

7. The process of claim 3, wherein the hydrocarbon radicals $R^{9a}$, $R^{9b}$ have from 1 to 10 carbon atoms.

8. The process of claim 4, wherein the hydrocarbon radicals $R^{9a}$, $R^{9b}$ have from 1 to 10 carbon atoms.

9. The process of claim 1, wherein the cocatalyst is one of the formula VI and VII, l and m are integers from 6 to 2000.

10. The process of claim 2, wherein the cocatalyst is one of the formula VI and VII, l and m are integers from 6 to 2000.

11. The process of claim 3, wherein the cocatalyst is one of the formula VI and VII, l and m are integers from 6 to 2000.

12. The process of claim 5, wherein the cocatalyst is one of the formula VI and VII, l and m are integers from 6 to 2000.

13. The process of claim 1, wherein the "en"compound in the formula IV has two double bonds.

14. The process of claim 9, wherein the "en"compound in the formula IV has two double bonds.

15. The process of claim 2, wherein the "en"compound in the formula IV has two double bonds.

16. The process of claim 1, further comprising separating a silane of the formula I by distillation, collecting a distillation bottoms comprising Ir-containing residues, and removing the bottoms as a catalyst in a further process for preparing silanes of the formula (I).

* * * * *